(12) United States Patent
Afar

(10) Patent No.: US 7,842,293 B2
(45) Date of Patent: Nov. 30, 2010

(54) COMPOSITIONS AND METHODS USING ANTI-CS1 ANTIBODIES TO TREAT MULTIPLE MYELOMA

(75) Inventor: Daniel Afar, Fremont, CA (US)

(73) Assignee: Facet Biotech Corporation, Redwood City, CA (US)

( * ) Notice: Subject to any disclaimer, the term of this patent is extended or adjusted under 35 U.S.C. 154(b) by 0 days.

(21) Appl. No.: 11/835,245

(22) Filed: Aug. 7, 2007

(65) Prior Publication Data

US 2008/0124332 A1 May 29, 2008

Related U.S. Application Data

(60) Provisional application No. 60/836,250, filed on Aug. 7, 2006, provisional application No. 60/856,144, filed on Nov. 1, 2006.

(51) Int. Cl.
 A61K 39/395 (2006.01)
 A61P 35/00 (2006.01)
 C12N 5/06 (2006.01)
(52) U.S. Cl. .................. 424/133.1; 424/138.1; 435/375
(58) Field of Classification Search .............. 424/133.1, 424/138.1; 435/375
 See application file for complete search history.

(56) References Cited

U.S. PATENT DOCUMENTS

| 2005/0025763 A1 | 2/2005 | Williams |
| 2006/0024296 A1 | 2/2006 | Williams |

FOREIGN PATENT DOCUMENTS

| WO | 2005/102387 A2 | 11/2005 |
| WO | 2008/019376 A2 | 2/2008 |
| WO | 2008/019378 A1 | 2/2008 |
| WO | 2008/019379 A2 | 2/2008 |

OTHER PUBLICATIONS

Yan et al. (Can. Res. 66(4):2305-2313 (2006).*
Koskela et al. (Leuk. Lymphoma 45(4):749-754 (2004) Abtract.*
Fundamental Immunology 242 (William E. Paul, M.D. ed., 3d ed. 1993).*
ATCC search for Luc63 antibody (pp. 1-3; May 11, 2009).*
Richardson et al., "A Phase 2 study of Bortezomib in relapsed,refractory myeloma," N Engl J Med, 348:2609-2617 (Jun. 2003).
Kumar and Rajkumar, "Thalidomide and lenalidomide in the treatment of multiple myeloma," European J Cancer, 42(2006):1612-1622, (Jul. 2006).
Tai et al., "Killing of drug-sensitive and resistant myeloma cells and disruption of their bone marrow stromal interaction by HuLuc63, a novel humanized anti-CS1 monoclonal antibody," Blood (ASH Annual Meeting Abstracts) 2006:108: Abstract 3470 (2006).
Richardson et al., "Immunomodulatory drug CC-5013 overcomes drug resistance and is well-tolerated in patients with relapsed multiple myeloma," Blood, 100(9):3063-3067 (Nov. 2002).

International Search Report and Written Opinion for PCT Application No. PCT/US2007/075404, dated Feb. 2, 2008.
International Search Report and Written Opinion for PCT Application No. PCT/US2007/075403, dated Jan. 16, 2008.
Tai et al., "Anti-CS1 humanized monoclonal antibody HuLuc63 inhibits myeloma cell adhesion and induces antibody-dependent cellular cytotoxicity in the bone marrow milieu." Blood, Oct. 9, 2007; [Epub ahead of print].
Afar et al., "Anti-myeloma activity of HuLuc63 alone and in combination with bortezomib." Haematologica 92 (6) s2:146, 2007. (Abstract PO-530).
Rice et al., "HuLuc63 in Combination Regimens with Conventional and Targeted Therapies Has Additive and Synergistic Anti-Tumor Activity in Pre-Clinical Models of Myeloma." Blood (ASH Annual Meeting Abstracts), Nov. 2007; 110:2517.
Sonneveld et al., "Changing concepts in multiple myeloma: from conventional chemotherapy to high-dose treatment" Eur J Cancer. Jan. 2003;39(1):9-18.
Jagannath S., "Treatment of myeloma in patients not eligible for transplantation." Curr Treat Options Oncol. May 2005;6(3):241-53.
Bruno et al., "New drugs for treatment of multiple myeloma." Lancet Oncol. Jul. 2004;5(7):430-42.
Lee et al., "DTPACE: an effective, novel combination chemotherapy with thalidomide for previously treated patients with myeloma." J Clin Oncol. Jul. 15, 2003;21(14):2732-9.
Boles et al., "Molecular cloning of CS1, a novel human natural killer cell receptor belonging to the CD2 subset of the immunoglobulin superfamily." Immunogenetics. 2001;52(3-4):302-7.
International Search Report and Written Opinion for PCT Application No. PCT/US2007/075401, dated May 15, 2008.
Anderson, Kenneth C., Lenalidomide and Thalidomide: Mechanisms of Action—Similarities and Differences, *Seminars in Hematology*, vol. 42, pp. S3-S8 (2005).
Bray et al., "Studies on the Mechanism of Human Natural Killer Cell-Mediated Cytolysis," *Cellular Immunology*, vol. 78, pp. 100-113 (1983).
Cavo et al., "Superiority of thalidomide and dexamethasone over vincristine-doxorubicindexamethasone (VAD) as primary therapy in preparation for autologous transplantation for multiple myeloma," *Blood*, vol. 106, pp. 35-39 (2005).
Liu et al., "Chimeric mouse-human IgG1 antibody that can mediate lysis of cancer cells," *Proc. Natl. Acad. Sci.*, vol. 84, pp. 3439-3443 (1987).
Piccolella et al., Effects of Dexamethasone on Human Natural Killer Cell Cytotoxicity, Interferon Production, and Interleukin-2 Receptor Expression Induced by Microbial Antigens, *Infection and Immunity*, vol. 51, No. 2, pp. 712-714 (1986).

\* cited by examiner

*Primary Examiner*—Lynn Bristol
(74) *Attorney, Agent, or Firm*—Dechert LLP

(57) ABSTRACT

The present disclosure provides methods for treating multiple myeloma comprising administering to a subject with multiple myeloma the anti-CS1 antibody HuLuc63 in combination with dexamethasone and, optionally, thalidomide.

7 Claims, 2 Drawing Sheets

COMPOSITIONS AND METHODS USING ANTI-CS1 ANTIBODIES TO TREAT MULTIPLE MYELOMA

1. CROSS REFERENCE TO RELATED APPLICATIONS

This application claims benefit under 35 U.S.C. §119(e) to application Ser. Nos. 60/836,250 filed Aug. 7, 2006 and 60/856,144 filed Nov. 1, 2006, the contents of which are incorporated herein by reference.

2. BACKGROUND

Multiple myeloma ("MM") represents a malignant proliferation of plasma cells derived from a single clone. The terms multiple myeloma and myeloma are used interchangeably to refer to the same condition. The myeloma tumor, its products, and the host response to it result in a number of organ dysfunctions and symptoms of bone pain or fracture, renal failure, susceptibility to infection, anemia, hypocalcemia, and occasionally clotting abnormalities, neurologic symptoms and vascular manifestations of hyperviscosity. See D. Longo, in Harrison's Principles of Internal Medicine 14th Edition, p. 713 (McGraw-Hill, New York, 1998). No effective long-term treatment currently exists for MM. It is a malignant disease of plasma cells, manifested as hyperproteinemia, anemia, renal dysfunction, bone lesions, and immunodeficiency. MM is difficult to diagnose early because there may be no symptoms in the early stage. The disease has a progressive course with a median duration of survival of six months when no treatment is given. Systemic chemotherapy is the main treatment, and the current median of survival with chemotherapy is about three years, however fewer than 5% live longer than 10 years (See Anderson, K. et al., *Annual Meeting Report* 1999. Recent Advances in the Biology and Treatment of Multiple Myeloma (1999)).

While multiple myeloma is considered to be a drug-sensitive disease, almost all patients who initially respond to chemotherapy eventually relapse (See Anderson, K. et al., *Annual Meeting Report* 1999. Recent Advances in the Biology and Treatment of Multiple Myeloma (1999)). Since the introduction of melphalan and prednisone therapy for MM, numerous multi-drug chemotherapies including Vinca alkaloid, anthracycline, and nitrosourea-based treatments have been tested (See Case, D C et al., (1977) Am. J. Med 63:897 903); however, there has been little improvement in outcome over the past three decades (See Case, D C et al., (1977) Am. J. Med 63:897 903; Otsuki, T. et al, (2000) Cancer Res. 60:1). New methods of treatment, such as combination therapies utilizing monoclonal antibodies, therapeutic agents, and small molecule inhibitors of cellular receptors and/or proteins implicated in MM, are needed.

3. SUMMARY

Described herein are compositions and methods useful for exploiting the anti-tumor properties of anti-CS1 antibodies. Anti-CS1 antibodies that can be used in the methods and compositions are described in U.S. Patent Publication Nos. 2005/0025763 and 2006/0024296, the contents of which are incorporated herein by reference. The anti-CS1 antibodies target CS1 (CD2-subset1), which is also known as SLAMF7, CRACC, 19A, APEX-1, and FOAP12 (Genbank Accession Number NM_021181.3). CS1, is a glycoprotein that is highly expressed in bone marrow samples from patients diagnosed with MM. In both in vitro and in vivo studies, anti-CS1 antibodies exhibit significant anti-myeloma activity (see, e.g., U.S. Patent Publication Nos. 2005/0025763 and 2006/0024296, the contents of which are incorporated herein by reference). By way of example, but not limitation, the anti-CS1 antibody, HuLuc63 effectively mediates lysis of myeloma cells via antibody dependent cellular cytotoxicity (ADCC) (see, e.g., U.S. Patent Publication No. 2005/0025763, the content of which is incorporated herein by reference). In a myeloma mouse tumor model, treatment with HuLuc63 significantly reduced tumor mass by more than 50% (see, e.g., U.S. Patent Publication No. 2005/0025763, the content of which is incorporated herein by reference).

The present disclosure relates to compositions and methods for treating patients diagnosed with Monoclonal Gammopathy of Undetermined Significance (MGUS), smoldering myeloma, asymptomatic MM, and symptomatic MM, ranging from newly diagnosed to late stage relapsed/refractory. In particular, the methods relate to the administration of a pharmaceutical composition comprising an anti-CS1 antibody in combination with one or more therapeutic agents. Anti-CS1 antibodies are typically administered intravenously at doses ranging from 0.5 to 20 mg/kg, from once a week to once a month.

One or more therapeutic agents, such as targeted agents, conventional chemotherapy agents, hormonal therapy agents, and supportive care agents and/or combinations thereof, can be administered concurrently, prior to, or following administration of an anti-CS1 antibody. The agents can be administered separately or combined in a cocktail and administered together as a single composition. The composition(s) can be administered by any means known in the art.

In some embodiments, administration of the pharmaceutical compositions described herein increases the sensitivity of multiple myeloma cells to a therapeutic agent. For example, inclusion of an anti-CS1 antibody, such as HuLuc63, enhances the activity of therapeutic agents, such that lower doses can be used in the compositions and methods described herein.

In some embodiments, administration of the pharmaceutical compositions described herein elicits at least one of the beneficial responses as defined by the European Group for Blood and Marrow transplantation (EBMT). For example, administration of the pharmaceutical compositions described herein can result in a complete response, partial response, minimal response, no change, or plateau.

4. BRIEF DESCRIPTION OF THE FIGURES

5. DETAILED DESCRIPTION

Figure 1:
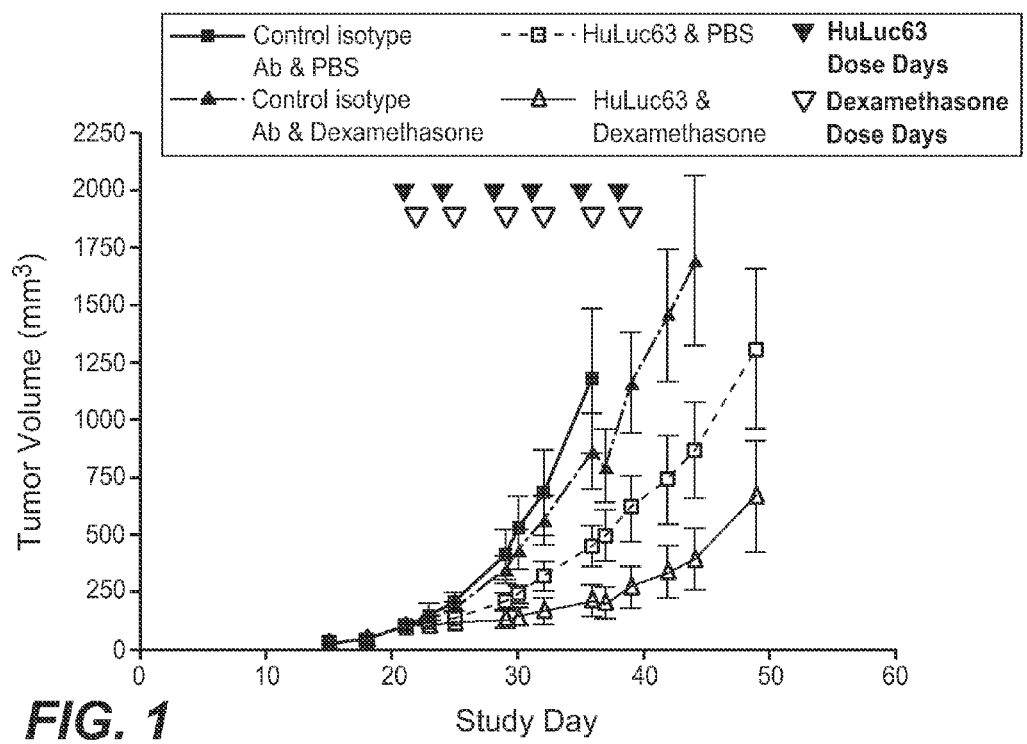
FIG. 1 depicts the anti-tumor activity of HuLuc63 alone and in combination with dexamethasone in an in vivo mouse multiple myeloma xenograft model.

The compositions described herein combine anti-CS1 antibodies with one or more therapeutic agents at specific doses to potentiate or complement the anti-myeloma activities of the other. Examples of suitable anti-CS1 antibodies include, but are not limited to, isolated antibodies that bind one or more of the three epitope clusters identified on CS1 and monoclonal antibodies produced by the hybridoma cell lines: Luc2, Luc3, Luc15, Luc22, Luc23, Luc29, Luc32, Luc34, Luc35, Luc37, Luc38, Luc39, Luc56, Luc60, Luc63, Luc69, LucX.1, LucX.2 or Luc90. These monoclonal antibodies are named as the antibodies: Luc2, Luc3, Luc15, Luc22, Luc23, Luc29, Luc32, Luc34, Luc35, Luc37, Luc38, Luc39, Luc56, Luc60, Luc63, Luc69, LucX and Luc90, respectively, hereafter. Humanized versions are denoted by the prefix "hu" (see, e.g., U.S. Patent Publication Nos. 2005/0025763 and 2006/0024296, the contents of which are incorporated herein by reference).

Plasmid pHuLuc63 encoding monoclonal antibody HuLuc63 was deposited with the American Type Culture Collection ("ATCC"), at 10801 University Blvd., Manassas, Va. 20510-209, U.S., on May 25, 2010. The deposited plasmid was assigned ATCC accession number PTA-10989.

In some embodiments, suitable anti-CS1 antibodies include isolated antibodies that bind one or more of the three epitope clusters identified on CS1 (SEQ ID NO: 1, Table 1 below; see, e.g., U.S. Patent Publication No. 2006/0024296, the content of which is incorporated herein by reference). As disclosed in U.S. Patent Publication No. 2006/0024296 and shown below in Table 1, the CS1 antibody binding sites have been grouped into 3 epitope clusters:

(1) the epitope defined by Luc90, which binds to hu50/mu50 (SEQ ID NO: 2). This epitope covers from about amino acid residue 23 to about amino acid residue 151 of human CS1. This epitope is resided within the domain 1 (V domain) of the extracellular domain. This epitope is also recognized by Luc34, LucX (including LucX.1 and LucX.2) and Luc69.
(2) the epitope defined by Luc38, which binds to mu25/hu75 (SEQ ID NO: 3) and hu50/mu50 (SEQ ID NO: 81). This epitope likely covers from about amino acid residue 68 to about amino acid residue 151 of human CS1. This epitope is also recognized by Luc5.
(3) the epitope defined by Luc 63, which binds to mu75/hu25 (SEQ ID NO: 4). This epitope covers from about amino acid residue 170 to about amino acid residue 227 of human CS1. This epitope is resided within domain 2 (C2 domain) of human CS1. This epitope is also recognized by Luc4, Luc12, Luc23, Luc29, Luc32 and Luc37.

The methods and pharmaceutical compositions are addressed in more detail below, but typically include at least one anti-CS1 antibody as described above. In some embodiments, the pharmaceutical compositions include the anti-CS1 antibody HuLuc63. HuLuc63 is a humanized recombinant monoclonal IgG1 antibody directed to human CS1. The amino acid sequence for the heavy chain variable region (SEQ ID NO: 5) and the light chain variable region (SEQ ID NO: 6) for HuLuc63 is disclosed in U.S. Patent Publication No. 2005/0025763, the content of which is incorporated herein by reference, and in Table 1.

TABLE 1

| SEQ ID NO: | Amino Acid Sequence |
|---|---|
| SEQ ID NO: 1 | Met Ala Gly Ser Pro Thr Cys Leu Thr Leu Ile Tyr Ile Leu Trp Gln Leu Thr Gly Ser Ala Ala Ser Gly Pro Val Lys Glu Leu Val Gly Ser Val Gly Gly Ala Val Thr Phe Pro Leu Lys Ser Lys Val Lys Gln Val Asp Ser Ile Val Trp Thr Phe Asn Thr Thr Pro Leu Val Thr Ile Gln Pro Glu Gly Gly Thr Ile Ile Val Thr Gln Asn Arg Asn Arg Glu Arg Val Asp Phe Pro Asp Gly Gly Tyr Ser Leu Lys Leu Ser Lys Leu Lys Ser Asn Asp Ser Gly Ile Tyr Tyr Val Gly Ile Tyr Ser Ser Ser Leu Gln Gln Pro Ser Thr Gln Glu Tyr Val Leu His Val Tyr Glu His Leu Ser Lys Pro Lys Val Thr Met Gly Leu Gln Ser Asn Lys Asn Gly Thr Cys Val Thr Asn Leu Thr Cys Cys Met Glu His Gly Glu Asp Val Ile Tyr Thr Trp Lys Ala Leu Gly Gln Ala Ala Asn Glu Ser His Asn Gly Ser Ile Leu Pro Ile Ser Trp Arg Trp Gly Glu Ser Asp Met Thr Phe Ile Cys Val Ala Arg Asn Pro Val Ser Arg Asn Phe Ser Ser Pro Ile Leu Ala Arg Lys Leu Cys Glu Gly Ala Ala Asp Asp Pro Asp Ser Ser Met Val Leu Leu Cys Leu Leu Leu Val Pro Leu Leu Leu Ser Leu Phe Val Leu Gly Leu Phe Leu Trp Phe Leu Lys Arg Glu Arg Gln Glu Glu Tyr Ile Glu Glu Lys Lys Arg Val Asp Ile Cys Arg Glu Thr Pro Asn Ile Cys Pro His Ser Gly Glu Asn Thr Glu Tyr Asp Thr Ile Pro His Thr Asn Arg Thr Ile Leu Lys Glu Asp Pro Ala Asn Thr Val Tyr Ser Thr Val Glu Ile Pro Lys Lys Met Glu Asn Pro His Ser Leu Leu Thr Met Pro Asp Thr Pro Arg Leu Phe Ala Tyr Glu Asn Val Ile |
| SEQ ID NO: 2 | Met Ala Gly Ser Pro Thr Cys Leu Thr Leu Ile Tyr Ile Leu Trp Gln Leu Thr Gly Ser Ala Ala Ser Gly Pro Val Lys Glu Leu Val Gly Ser Val Gly Gly Ala Val Thr Phe Pro Leu Lys Ser Lys Val Lys Gln Val Asp Ser Ile Val Trp Thr Phe Asn Thr Thr Pro Leu Val Thr Ile Gln Pro Glu Gly Gly Thr Ile Ile Val Thr Gln Asn Arg Asn Arg Glu Arg Val Asp Phe Pro Asp Gly Gly Tyr Ser Leu Lys Leu Ser Lys Leu Lys Ser Asn Asp Ser Gly Ile Tyr Tyr Val Gly Ile Tyr Ser Ser Ser Leu Gln Gln Pro Ser Thr Gln Glu Tyr Val Leu His Val Tyr Glu His Leu Ser Lys Pro Lys Val Thr Ile Asp Arg Gln Ser Asn Lys Asn Gly Thr Cys Val Ile Asn Leu Thr Cys Ser Thr Asp Gln Asp Gly Glu Asn Val Thr Tyr Ser Trp Lys Ala Val Gly Gln Gly Gly Asp Asn Gln Phe His Asp Gly Ala Thr Leu Ser Ile Ala Trp Arg Ser Gly Glu Lys Asp Gln Ala Leu Thr Cys Met Ala Arg Asn Pro Val Ser Asn Ser Phe Ser Thr Pro Val Phe Pro Gln Lys Leu Cys Glu Asp Ala Ala Thr Asp Leu Thr Ser Leu Arg Gly |
| SEQ ID NO: 3 | Met Ala Arg Phe Ser Thr Tyr Ile Ile Phe Thr Ser Val Leu Cys Gln Leu Thr Val Thr Ala Ala Ser Gly Thr Leu Lys Lys Val Ala Gly Ala Leu Asp Gly Ser Val Thr Phe Thr Leu Asn Ile Thr Glu Ile Lys Val Asp Tyr Val Val Trp Thr Phe Asn Thr Phe Phe Leu Ala Met Val Lys Lys Asp Gly Gly |

TABLE 1-continued

| SEQ ID NO: | Amino Acid Sequence |
|---|---|
| | Thr Ile Ile Val Thr Gln Asn Arg Asn Arg Glu Arg Val Asp Phe Pro Asp
Gly Gly Tyr Ser Leu Lys Leu Ser Lys Leu Lys Asn Asp Ser Gly Ile
Tyr Tyr Val Gly Ile Tyr Ser Ser Ser Leu Gln Gln Pro Ser Thr Gln Glu Tyr
Val Leu His Val Tyr Glu His Leu Ser Lys Pro Lys Val Thr Met Gly Leu
Gln Ser Asn Lys Asn Gly Thr Cys Val Thr Asn Leu Thr Cys Cys Met Glu
His Gly Glu Glu Asp Val Ile Tyr Thr Trp Lys Ala Leu Gly Gln Ala Ala
Asn Glu Ser His Asn Gly Ser Ile Leu Pro Ile Ser Trp Arg Trp Gly Glu Ser
Asp Met Thr Phe Ile Cys Val Ala Arg Asn Pro Val Ser Arg Asn Phe Ser
Ser Pro Ile Leu Ala Arg Lys Leu Cys Glu Gly Ala Ala Asp Asp Pro Asp
Ser Ser Met Val |
| SEQ ID NO: 4 | Met Ala Arg Phe Ser Thr Tyr Ile Ile Phe Thr Ser Val Leu Cys Gln Leu
Thr Val Thr Ala Ala Ser Gly Thr Leu Lys Lys Val Ala Gly Ala Leu Asp
Gly Ser Val Thr Phe Thr Leu Asn Ile Thr Glu Ile Lys Val Lys Asp Tyr Val
Val Trp Thr Phe Asn Thr Phe Phe Leu Ala Met Val Lys Lys Asp Gly Val
Thr Ser Gln Ser Ser Asn Lys Glu Arg Ile Val Phe Pro Asp Gly Leu Tyr
Ser Met Lys Leu Ser Gln Leu Lys Lys Asn Asp Ser Gly Ala Tyr Arg Ala
Glu Ile Tyr Ser Thr Ser Ser Gln Ala Ser Leu Ile Gln Glu Tyr Val Leu His
Val Tyr Lys His Leu Ser Arg Pro Lys Val Thr Ile Asp Arg Gln Ser Asn
Lys Asn Gly Thr Cys Val Ile Asn Leu Thr Cys Ser Thr Asp Gln Asp Gly
Glu Asn Val Thr Tyr Ser Trp Lys Ala Val Gly Gln Ala Ala Asn Glu Ser
His Asn Gly Ser Ile Leu Pro Ile Ser Trp Arg Trp Gly Glu Ser Asp Met
Thr Phe Ile Cys Val Ala Arg Asn Pro Val Ser Arg Asn Phe Ser Ser Pro
Ile Leu Ala Arg Lys Leu Cys Glu Gly Ala Ala Asp Asp Pro Asp Ser Ser
Met Val |
| SEQ ID NO: 5 | Glu Val Gln Leu Val Glu Ser Gly Gly Gly Leu Val Gln Pro Gly Gly Ser
Leu Arg Leu Ser Cys Ala Ala Ser Gly Phe Asp Phe Ser Arg Tyr Trp Met
Ser Trp Val Arg Gln Ala Pro Gly Lys Gly Leu Glu Trp Ile Gly Glu Ile
Asn Pro Asp Ser Ser Thr Ile Asn Tyr Ala Pro Ser Leu Lys Asp Lys Phe
Ile Ile Ser Arg Asp Asn Ala Lys Asn Ser Leu Tyr Leu Gln Met Asn Ser
Leu Arg Ala Glu Asp Thr Ala Val Tyr Tyr Cys Ala Arg Pro Asp Gly Asn
Tyr Trp Tyr Phe Asp Val Trp Gly Gln Gly Thr Leu Val Thr Val Ser Ser |
| SEQ ID NO: 6 | Asp Ile Gln Met Thr Gln Ser Pro Ser Ser Leu Ser Ala Ser Val Gly Asp
Arg Val Thr Ile Thr Cys Lys Ala Ser Gln Asp Val Gly Ile Ala Val Ala
Trp Tyr Gln Gln Lys Pro Gly Lys Val Pro Lys Leu Leu Ile Tyr Trp Ala
Ser Thr Arg His Thr Gly Val Pro Asp Arg Phe Ser Gly Ser Gly Ser Gly
Thr Asp Phe Thr Leu Thr Ile Ser Ser Leu Gln Pro Glu Asp Val Ala Thr
Tyr Tyr Cys Gln Gln Tyr Ser Ser Tyr Pro Tyr Thr Phe Gly Gln Gly Thr
Lys Val Glu Ile Lys |

At some doses, additive effects are seen; at other doses, synergistic effects are seen. In some embodiments, the synergistic effect permits one or more therapeutic agents to be administered in combination with one or more anti-CS1 antibodies at a reduced dosage, while retaining efficacy. Given that the side effects associated with the use of these agents are dose-dependent, use of the compositions and methods described herein can reduce the deleterious side effects observed in conventional and novel treatment regimens used to treat MM when these agents are administered at their recommended dosages.

In other embodiments, the synergistic effect permits one or more therapeutic agents to be administered in combination with one or more anti-CS1 antibodies at the approved dosage, but with greater than the expected efficacy.

The compositions can be administered for the treatment of Monoclonal Gammopathy of Undetermined Significance (MGUS), smoldering myeloma, asymptomatic MM, and symptomatic MM, ranging from newly diagnosed to late stage relapsed/refractory. Typically, administration of the compositions results in a reduction in M-protein in serum or urine such that a plateau, no change, minimal, partial or complete response is observed as defined by the European Group for Blood and Marrow transplantation (EBMT).

5.2 Pharmaceutical Compositions

Provided herein are pharmaceutical compositions that are beneficial in reducing tumor mass and/or regressing tumor growth, in patients diagnosed with multiple myeloma. In addition, the pharmaceutical compositions can be used to treat other diseases characterized by the presence of monoclonal protein (M-protein, paraprotein) in the serum or urine.

In some embodiments, the various components of the compositions are provided separately. For example, an anti-CS1 antibody can be provided in a first pharmaceutical composition, and a therapeutic agent provided in a second composition. When the composition comprises two or more therapeutic agents, an anti-CS1 antibody can be provided in a first pharmaceutical composition, one therapeutic agent can be provided in a second composition and the other therapeutic agent can be provided in a third composition. In other embodiments, an anti-CS1 antibody can be provided in one pharmaceutical composition and the therapeutic agents can be combined and provided in a second pharmaceutical composition. In still other embodiments, one composition, comprising an anti-CS1 antibody and one or more therapeutic agents can be provided.

In typical embodiments, an anti-CS1 antibody is present in a pharmaceutical composition at a concentration sufficient to permit intravenous administration at 0.5 mg/kg to 20 mg/kg. In some embodiments, the concentration of an anti-CS1 antibody suitable for use in the compositions and methods described herein includes, but is not limited to, at least about 0.5 mg/kg, at least about 0.75 mg/kg, at least about 1 mg/kg, at least about 2 mg/kg, at least about 2.5 mg/kg, at least about 3 mg/kg, at least about 4 mg/kg, at least about 5 mg/kg, at least about 6 mg/kg, at least about 7 mg/kg, at least about 8 mg/kg, at least about 9 mg/kg, at least about 10 mg/kg, at least about 11 mg/kg, at least about 12 mg/kg, at least about 13 mg/kg, at least about 14 mg/kg, at least about 15 mg/kg, at least about 16 mg/kg, at least about 17 mg/kg, at least about 18 mg/kg, at least about 19 mg/kg, and at least about 20 mg/kg.

The anti-CS1 antibodies can be administered in single or multiple dose regimens. Generally, an anti-CS1 antibody is administered over a period of time from about 1 to about 24 hours, but is typically administered over a period of about 1 to 2 hours. Dosages can be repeated from about 1 to about 4 weeks or more, for a total of 4 or more doses. Typically, dosages are repeated once every week, once every other week, or once a month for a minimum of 4 doses to a maximum of 52 doses.

Determination of the effective dosage, total number of doses, and length of treatment with an anti-CS1 antibody is well within the capabilities of those skilled in the art, and can be determined using a standard dose escalation study to identify the maximum tolerated dose (MTD) (see, e.g., Richardson et al., 2002, Blood, 100(9):3063-3067, the content of which is incorporated herein by reference).

In some embodiments, one or more therapeutic agents are administered in combination with an anti-CS1 antibody. The agents can be administered concurrently, prior to, or following administration of an anti-CS1 antibody.

In some embodiments, an anti-CS1 antibody is administered prior to the administration of the therapeutic agents. For example, the anti-CS1 antibody can be administered approximately 0 to 60 days prior to the administration of the therapeutic agents. In some embodiments, an anti-CS1 antibody, such as HuLuc63, is administered from about 30 minutes to about 1 hour prior to the administration of the therapeutic agents, or from about 1 hour to about 2 hours prior to the administration of the therapeutic agents, or from about 2 hours to about 4 hours prior to the administration of the therapeutic agents, or from about 4 hours to about 6 hours prior to the administration of the therapeutic agents, or from about 6 hours to about 8 hours prior to the administration of the therapeutic agents, or from about 8 hours to about 16 hours prior to the administration of the therapeutic agents, or from about 16 hours to 1 day prior to the administration of the therapeutic agents, or from about 1 to 5 days prior to the administration of the therapeutic agents, or from about 5 to 10 days prior to the administration of the therapeutic agents, or from about 10 to 15 days prior to the administration of the therapeutic agents, or from about 15 to 20 days prior to the administration of the therapeutic agents, or from about 20 to 30 days prior to the administration of the therapeutic agents, or from about 30 to 40 days prior to the administration of the therapeutic agents, and from about 40 to 50 days prior to the administration of the therapeutic agents, or from about 50 to 60 days prior to the administration of the therapeutic agents.

In some embodiments, the anti-CS1 antibody is administered concurrently with the administration of the therapeutic agents.

In some embodiments, an anti-CS1 antibody is administered following the administration of the therapeutic agents. For example, an anti-CS1 antibody, such as HuLuc63, can be administered approximately 0 to 60 days after the administration of the therapeutic agents. In some embodiments, HuLuc63 is administered from about 30 minutes to about 1 hour following the administration of the therapeutic agents, or from about 1 hour to about 2 hours following the administration of the therapeutic agents, or from about 2 hours to about 4 hours following the administration of the therapeutic agents, or from about 4 hours to about 6 hours following the administration of the therapeutic agents, or from about 6 hours to about 8 hours following the administration of the therapeutic agents, or from about 8 hours to about 16 hours following the administration of the therapeutic agents, or from about 16 hours to 1 day following the administration of the therapeutic agents, or from about 1 to 5 days following the administration of the therapeutic agents, or from about 5 to 10 days following the administration of the therapeutic agents, or from about 10 to 15 days following the administration of the therapeutic agents, or from about 15 to 20 days following the administration of the therapeutic agents, or from about 20 to 30 days following the administration of the therapeutic agents, or from about 30 to 40 days following the administration of the therapeutic agents, and from about 40 to 50 days following the administration of the therapeutic agents, or from about 50 to 60 days following the administration of the therapeutic agents.

Therapeutic agents that can be used in combination with the anti-CS1 antibodies described herein include, but are not limited to, targeted agents, conventional chemotherapy agents, hormonal therapy agents, and supportive care agents. One or more therapeutic agents from the different classes, e.g., targeted, conventional chemotherapeutic, hormonal, and supportive care, and/or subclasses can be combined in the compositions described herein. The various classes described herein can be further divided into subclasses. By way of example, targeted agents can be separated into a number of different subclasses depending on their mechanism of action. As will be apparent to those of skill in the art, the agents can have more than one mechanism of action, and thus, could be classified into one or more subclasses. For purposes of the compositions and methods described herein, the following subclasses have been identified: anti-angiogenic, inhibitors of growth factor signaling, immunomodulators, inhibitors of protein synthesis, folding and/or degradation, inhibitors of gene expression, pro-apoptotic agents, agents that inhibit signal transduction and agents with "other" mechanisms of action. Typically, the mechanism of action for agents falling into the "other" subclass is unknown or poorly characterized.

For example, in some embodiments, targeted agents, such as bevacizumab, sutinib, sorafenib, 2-methoxyestradiol or 2ME2, finasunate, PTK787, vandetanib, aflibercept, volociximab, etaracizumab (MEDI-522), cilengitide, erlotinib, cetuximab, panitumumab, gefitinib, trastuzumab, TKI258, CP-751,871, atacicept, rituximab, alemtuzumab, aldesleukine, atlizumab, tocilizumab, temsirolimus, everolimus, NPI-1387, MLNM3897, HCD122, SGN-40, HLL1, huN901-DM1, atiprimod, natalizumab, bortezomib, carfilzomib, NPI-0052, tanespimycin, saquinavir mesylate, ritonavir, nelfinavir mesylate, indinavir sulfate, belinostat, LBH589, mapatumumab, lexatumumab, AMG951, ABT-737, oblimersen, plitidepsin, SCIO-469, P276-00, enzastaurin, tipifamib, perifosine, imatinib, dasatinib, lenalidomide, thalidomide, simvastatin, and celecoxib can be combined with an anti-CS1 antibody, such as HuLuc63 and used to treat MM patients.

By way of another example, conventional chemotherapy agents, such as alklyating agents (e.g., oxaliplatin, carboplatin, cisplatin, cyclophosphamide, melphalan, ifosfamide, uramustine, chlorambucil, carmustine, mechloethamine, thiotepa, busulfan, temozolomide, dacarbazine), anti-metabolic agents (e.g., gemcitabine, cytosine arabinoside, Ara-C, capecitabine, 5FU (5-fluorouracil), azathioprine, mercaptopurine (6-MP), 6-thioguanine, aminopterin, pemetrexed, methotrexate), plant alkaloid and terpenoids (e.g., docetaxel, paclitaxel, vincristine, vinblastin, vinorelbine, vindesine, etoposide, VP-16, teniposide, irinotecan, topotecan), anti-tumor antibiotics (e.g., dactinomycin, doxorubicin, liposomal doxorubicin, daunorubicin, daunomycin, epirubicin, mitoxantrone, adriamycin, bleomycin, plicamycin, mitomycin C, caminomycin, esperamicins), and other agents (e.g., darinaparsin) can be combined with an anti-CS1 antibody, such as HuLuc63 and used to treat MM.

By way of another example, hormonal agents such as anastrozole, letrozole, goserelin, tamoxifen, dexamethasone, prednisone, and prednisilone can be combined with an anti-CS1 antibody, such as HuLuc63 and used to treat MM.

By way of another example, supportive care agents such as pamidronate, zoledonic acid, ibandronate, gallium nitrate, denosumab, darbepotin alpha, epoetin alpha, eltrombopag, and pegfilgrastim can be combined with an anti-CS1 antibody, such as HuLuc63 and used to treat MM.

The therapeutic agents can be administered in any manner found appropriate by a clinician and are typically provided in generally accepted efficacious dose ranges, such as those described in the Physician Desk Reference, 56th Ed. (2002), Publisher Medical Economics, New Jersey. In other embodiments, a standard dose escalation study can be performed to identify the maximum tolerated dose (MTD) (see, e.g., Richardson, et al. 2002, Blood, 100(9):3063-3067, the content of which is incorporated herein by reference).

In some embodiments, doses less than the generally accepted efficacious dose of a therapeutic agent can be used. For example, in various embodiments, the composition comprises a dosage that is less than about 10% to 75% of the generally accepted efficacious dose range. In some embodiments, at least about 10% or less of the generally accepted efficacious dose range is used, at least about 15% or less, at least about 25%, at least about 30% or less, at least about 40% or less, at least about 50% or less, at least about 60% or less, at least about 75% or less, and at least about 90%.

The therapeutic agents can be administered singly or sequentially, or in a cocktail with other therapeutic agents, as described below. The therapeutic agents can be administered orally, intravenously, systemically by injection intramuscularly, subcutaneously, intrathecally or intraperitoneally.

In some embodiments, the therapeutic agents provided in the pharmaceutical composition(s) are selected from the group consisting of dexamethasone, thalidomide, vincristine, carmustine (BCNU), melphalan, cyclophosphamide, prednisone, doxorubicin, cisplatin, etoposide, bortezomib, lenalidomide, ara-C, and/or combinations thereof.

In certain embodiments, however, the pharmaceutical composition does not comprise bortezomib and/or lenalidomide.

Accordingly, in some embodiments, two pharmaceutical compositions are provided: a first comprising a therapeutically effective amount of an anti-CS1 antibody such as HuLuc63 and a second comprising a therapeutically effective amount of dexamethasone.

In some embodiments, at least two pharmaceutical compositions are provided: a first comprising a therapeutically effective amount of an anti-CS1 antibody such as HuLuc63 and a second comprising a therapeutically effective amount of dexamethasone and thalidomide. In some embodiments, dexamethasone and thalidomide are provided separately, such that a total of three pharmaceutical compositions are provided: a first comprising an anti-CS1 antibody such as HuLuc63, a second comprising dexamethasone, and a third comprising thalidomide.

In some embodiments, at least two pharmaceutical compositions are provided: a first comprising a therapeutically effective amount of an anti-CS1 antibody such as HuLuc63 and a second comprising a therapeutically effective amount of vincristine, doxorubicin and dexamethasone (e.g., VAD). In some embodiments, vincristine, doxorubicin and dexamethasone are provided separately. Provided that the agents retain their efficacy, compositions comprising other combinations of agents can be prepared depending in part, on dosage, route of administration, and whether the agents are provided in a solid, semi-solid or liquid form. For example, a total of three compositions can be made: a first comprising a therapeutically effective amount of an anti-CS1 antibody such as HuLuc63, a second comprising dexamethasone, and a third comprising vincristine and doxorubicin.

In some embodiments, at least two pharmaceutical compositions are provided: a first comprising a therapeutically effective amount of an anti-CS1 antibody such as HuLuc63 and a second comprising a therapeutically effective amount of doxorubicin HCl liposome injection, vincristine and dexamethasone (e.g., DVd). Provided that the agents retain their efficacy, compositions comprising other combinations of agents can be prepared depending in part, on dosage, route of administration, and whether the agents are provided in a solid, semi-solid or liquid form. For example, a total of three compositions can be made: a first comprising a therapeutically effective amount of an anti-CS1 antibody such as HuLuc63, a second comprising doxorubicin HCl liposome injection, and a third comprising vincristine and dexamethasone.

In some embodiments, two pharmaceutical compositions are provided: a first comprising a therapeutically effective amount of an anti-CS1 antibody such as HuLuc63 and a second comprising a therapeutically effective amount of cyclophosphamide.

In some embodiments, at least two pharmaceutical compositions are provided: a first comprising a therapeutically effective amount of an anti-CS1 antibody such as HuLuc63 and a second comprising a therapeutically effective amount of dexamethasone, thalidomide, cisplatin, doxorubicin, cyclophosphamide and etoposide (e.g., DT-PACE). Provided that the agents retain their efficacy, compositions comprising other combinations can be prepared depending in part, on dosage, route of administration, and whether the agents are provided in a solid, semi-solid or liquid form. By way of example, dexamethasone and thalidomide could be provided in one composition and cisplatin, doxorubicin, cyclophosphamide and etoposide provided in another composition.

In some embodiments, at least two pharmaceutical compositions are provided: a first comprising a therapeutically effective amount of an anti-CS1 antibody such as HuLuc63 and a second comprising a therapeutically effective amount of vincristine, doxorubicin, dexamethasone, and cyclophosphamide. Provided that the agents retain their efficacy, compositions comprising other combinations can be prepared depending in part, on dosage, route of administration, and whether the agents are provided in a solid, semi-solid or liquid form. By way of example, vincristine, doxorubicin, and cyclophosphamide could be provided as one composition and dexamethasone as a second.

In some embodiments, at least two pharmaceutical compositions are provided: a first comprising a therapeutically effective amount of an anti-CS1 antibody such as HuLuc63 and a second comprising a therapeutically effective amount of doxorubicin HCl liposome injection, vincristine, dexamethasone, and thalidomide. Provided that the agents retain their efficacy, compositions comprising other combinations can be prepared depending in part, on dosage, route of administration, and whether the agents are provided in a solid, semi-solid or liquid form. By way of example, vincristine, dexamethasone, and thalidomide could be provided as one composition and doxorubicin HCl liposome injection as a second.

In some embodiments, at least two pharmaceutical compositions are provided: a first comprising a therapeutically effective amount of an anti-CS1 antibody such as HuLuc63 and a second comprising a therapeutically effective amount of doxorubicin HCl liposome injection and bortezomib. Provided that the agents retain their efficacy, compositions comprising other combinations can be prepared depending in part, on dosage, route of administration, and whether the agents are provided in a solid, semi-solid or liquid form. By way of example, doxorubicin HCl liposome injection can be provided as one composition and bortezomib as a second.

In some embodiments, agents with the same mechanism of action as an anti-CS1 antibody, such as HuMax-Cd38 (Genmab) can be provided in the pharmaceutical compositions described herein.

In some embodiments, the pharmaceutical compositions comprise therapeutic agents with a mechanism of action that differs from an anti-CS1 antibody. For example, targeted agents that inhibit angiogenesis, including, but not limited to, bevacizumab, sutinib, sorafenib, 2-methoxyestradiol or 2ME2, finasunate, PTK787, vandetanib, aflibercept, volociximab, etaracizumab (MEDI-522), cilengitide, can be used in the pharmaceutical compositions described herein. In other embodiments, agents that inhibit growth factor signaling, including, but not limited to, erlotinib, cetuximab, panitumumab, gefitinib, trastuzumab, TKI258, CP-751,871, atacicept, can be used in the pharmaceutical compositions described herein. In other embodiments, immunomodulators including, but not limited to, rituximab, alemtuzumab, aldesleukine, atlizumab, tocilizumab, temsirolimus, everolimus, NPI-1387, MLNM3897, HCD122, SGN-40, HLL1, huN901-DM1, atiprimod, natalizumab, can be used in the pharmaceutical compositions described herein. In other embodiments, agents that inhibit protein synthesis, folding or degradation, including but not limited to, bortezomib, carfilzomib, NPI-0052, tanespimycin, saquinavir mesylate, ritonavir, nelfinavir mesylate, indinavir sulfate, can be used in the pharmaceutical compositions described herein. In other embodiments, agents that inhibit gene expression including but not limited to, belinostat, LBH589, can be used in the pharmaceutical compositions described herein. In other embodiments, pro-apoptotic agents including but not limited to, mapatumumab, lexatumumab, AMG951, ABT-737, oblimersen, plitidepsin, can be used in the pharmaceutical compositions described herein. In other embodiments, agents that inhibit signal transduction including but not limited to, SCIO-469, P276-00, enzastaurin, tipifarnib, perifosine, imatinib, can be used in the pharmaceutical compositions described herein. In other embodiments, agents with other mechanisms of action including but not limited to, dasatinib, lenalidomide, thalidomide, simvastatin, and celecoxib can be used in the pharmaceutical compositions described herein.

The pharmaceutical compositions can exist as a solid, semi-solid, or liquid (e.g., suspensions or aerosols) dosage form. Typically, the compositions are administered in unit dosage forms suitable for single administration of precise dosage amounts. For example, an anti-CS1 antibody can be packaged in dosages ranging from about 1 to 1000 mg. In some embodiments, an anti-CS1 antibody is packaged in a dosage at least about 1 mg, at least about 10 mg, at least about 20 mg, at least about 50 mg, at least about 100 mg, at least about 200 mg, at least about 300 mg, at least about 400 mg, at least about 500 mg, at least about 750 mg, at least about 1000 mg.

The compositions can also include, depending on the formulation desired, pharmaceutically-acceptable, nontoxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution.

In addition, the pharmaceutical composition or formulation can also include other carriers, adjuvants, or nontoxic, non-therapeutic, nonimmunogenic stabilizers and the like. Effective amounts of such diluent or carrier will be those amounts that are effective to obtain a pharmaceutically acceptable formulation in terms of solubility of components, or biological activity.

5.3 Use of the Pharmaceutical Compositions to Treat Multiple Myeloma

The pharmaceutical compositions described herein find use in treating MM. Typically, the compositions can be used to treat Monoclonal Gammopathy of Undetermined Significance (MGUS), smoldering myeloma, asymptomatic MM, and symptomatic MM, ranging from newly diagnosed to late stage relapsed/refractory.

The compositions can be combined with other treatment strategies, i.e., autologous stem cell transplantation and allogeneic effector cell transplantation, to develop an effective treatment strategy based on the stage of myeloma being treated (see, e.g., Multiple Myeloma Research Foundation, Multiple Myeloma: Stem Cell Transplantation 1-30 (2004); U.S. Pat. Nos. 6,143,292, and 5,928,639, Igarashi, et al. Blood 2004, 104(1): 170-177, Maloney, et al. 2003, Blood, 102(9): 3447-3454, Badros, et al. 2002, J Clin Oncol., 20:1295-1303, Tricot, et al. 1996, Blood, 87(3):1196-1198; the contents of which are incorporated herein by reference).

The staging system most widely used since 1975 has been the Durie-Salmon system, in which the clinical stage of disease (Stage I, II, or III) is based on four measurements (see, e.g., Durie and Salmon, 1975, Cancer, 36:842-854). These four measurements are: (1) levels of monoclonal (M) protein (also known as paraprotein) in the serum and/or the urine; (2) the number of lytic bone lesions; (3) hemoglobin values; and, (4) serum calcium levels. These three stages can be further divided according to renal function, classified as A (relatively normal renal function, serum creatinine value<2.0 mg/dL) and B (abnormal renal function, creatinine value≧2.0 mg/dL). A new, simpler alternative is the International Staging System (ISS) (see, e.g., Greipp et al., 2003, "Development of an international prognostic index (IPI) for myeloma: report of the international myeloma working group", The Hematology). The ISS is based on the assessment of two blood test results, beta$_2$-microglobulin ($\beta_2$-M) and albumin, which separates patients into three prognostic groups irrespective of type of therapy.

Administration of the pharmaceutical compositions at selected dosage ranges and routes typically elicits a beneficial response as defined by the European Group for Blood and Marrow transplantation (EBMT). Table 2 lists the EBMT criteria for response.

TABLE 2

EBMT/IBMTR/ABMTR[1] Criteria for Response

| | |
|---|---|
| Complete Response | No M-protein detected in serum or urine by immunofixation for a minimum of 6 weeks and fewer than 5% plasma cells in bone marrow |

TABLE 2-continued

EBMT/IBMTR/ABMTR[1] Criteria for Response

| | |
|---|---|
| Partial Response | >50% reduction in serum M-protein level and/or 90% reduction in urine free light chain excretion or reduction to <200 mg/24 hrs for 6 weeks[2] |
| Minimal Response | 25-49% reduction in serum M-protein level and/or 50-89% reduction in urine free light chain excretion which still exceeds 200 mg/24 hrs for 6 weeks[3] |
| No Change | Not meeting the criteria or either minimal response or progressive disease |
| Plateau | No evidence of continuing myeloma-related organ or tissue damage, <25% change in M-protein levels and light chain excretion for 3 months |
| Progressive Disease | Myeloma-related organ or tissue damage continuing despite therapy or its reappearance in plateau phase, >25% increase in serum M-protein level (>5 g/L) and/or >25% increase in urine M-protein level (>200 mg/24 hrs) and/or >25% increase in bone marrow plasma cells (at least 10% in absolute terms)[2] |
| Relapse | Reappearance of disease in patients previously in complete response, including detection of paraprotein by immunofixation |

[1]EBMT: European Group for Blood and Marrow transplantation; IBMTR: International Bone Marrow Transplant Registry; ABMTR: Autologous Blood and Marrow Transplant Registry.
[2]For patients with non-secretory myeloma only, reduction of plasma cells in the bone marrow by >50% of initial number (partial response) or 25-49% of initial number (minimal response) is required.
[3]In non-secretory myeloma, bone marrow plasma cells should increase by >25% and at least 10% in absolute terms; MRI examination may be helpful in selected patients.

Additional criteria that can be used to measure the outcome of a treatment include "near complete response" and "very good partial response". A "near complete response" is defined as the criteria for a "complete response" (CR), but with a positive immunofixation test. A "very good partial response" is defined as a greater than 90% decrease in M protein (see, e.g., Multiple Myeloma Research Foundation, Multiple Myeloma: Treatment Overview 9 (2005)).

The degree to which administration of the compositions elicits a response in an individual clinically manifesting at least one symptom associated with MM, depends in part, on the severity of disease, e.g., Stage I, II, or III, and in part, on whether the patient is newly diagnosed or has late stage refractory MM. Thus, in some embodiments, administration of the pharmaceutical composition elicits a complete response.

In other embodiments, administration of the pharmaceutical composition elicits a very good partial response or a partial response.

In other embodiments, administration of the pharmaceutical composition elicits a minimal response.

In other embodiments, administration of the pharmaceutical composition prevents the disease from progressing, resulting in a response classified as "no change" or "plateau" by the EBMT.

Routes of administration and dosage ranges for compositions comprising an anti-CS1 antibody such as HuLuc63 and one or more therapeutic agents for treating individuals diagnosed with MM, can be determined using art-standard techniques, such as a standard dose escalation study to identify the MTD (see, e.g., Richardson, et al. 2002, Blood, 100(9):3063-3067, the content of which is incorporated herein by reference).

Typically, anti-CS1 antibodies are administered intravenously. Administration of the other therapeutic agents described herein can be by any means known in the art. Such means include oral, rectal, nasal, topical (including buccal and sublingual) or parenteral (including subcutaneous, intramuscular, intravenous and intradermal) administration and will depend in part, on the available dosage form. For example, therapeutic agents that are available in a pill or capsule format typically are administered orally. However, oral administration generally requires administration of a higher dose than does intravenous administration. Determination of the actual route of administration that is best in a particular case is well within the capabilities of those skilled in the art, and in part, will depend on the dose needed versus the number of times per month administration is required.

Factors affecting the selected dosage of an anti-CS1 antibody and the therapeutic agents used in the compositions and methods described herein, include, but are not limited to, the type of agent, the age, weight, and clinical condition of the recipient patient, and the experience and judgment of the clinician or practitioner administering the therapy. Generally, the selected dosage should be sufficient to result in no change, but preferably results in at least a minimal change. An effective amount of a pharmaceutical agent is that which provides an objectively identifiable response, e.g., plateau, no change, minimal, partial, or complete, as noted by the clinician or other qualified observer, and as defined by the EBMT.

Generally, an anti-CS1 antibody is administered as a separate composition from the composition(s) comprising the therapeutic agents. As discussed above, the therapeutic agents can each be administered as a separate composition, or combined in a cocktail and administered as a single combined composition. In some embodiments, the compositions comprising an anti-CS1 antibody and one or more therapeutic agents are administered concurrently. In other embodiments, an anti-CS1 antibody can be administered prior to the administration of composition(s) comprising the therapeutic agent(s). In yet other embodiments, an anti-CS1 antibody is administered following the administration of composition(s) comprising the therapeutic agent(s).

In those embodiments in which the an anti-CS1 antibody is administered prior to or following the administration of the therapeutic agents, determination of the duration between the administration of an anti-CS1 antibody and administration of the agents is well within the capabilities of those skilled in the art, and in part, will depend on the dose needed versus the number of times per month administration is required.

Doses of anti-CS1 antibodies used in the methods described herein typically range between 0.5 mg/kg to 20 mg/kg. Optimal doses for the therapeutic agents are the generally accepted efficacious doses, such as those described in the Physician Desk Reference, 56th Ed. (2002), Publisher Medical Economics, New Jersey. Optimal doses for agents not described in the Physician Desk Reference can be determined using a standard dose escalation study to identify the MTD (see, e.g., Richardson, et al. 2002, Blood, 100(9):3063-3067, the contents of which are incorporated herein by reference).

In some embodiments, an anti-CS1 antibody is present in a pharmaceutical composition at a concentration, or in a weight/volume percentage, or in a weight amount, suitable for intravenous administration at a dosage rate at least about 0.5 mg/kg, at least about 0.75 mg/kg, at least about 1 mg/kg, at least about 2 mg/kg, at least about 2.5 mg/kg, at least about 3 mg/kg, at least about 4 mg/kg, at least about 5 mg/kg, at least about 6 mg/kg, at least about 7 mg/kg, at least about 8 mg/kg, at least about 9 mg/kg, at least about 10 mg/kg, at least about 11 mg/kg, at least about 12 mg/kg, at least about 13 mg/kg, at least about 14 mg/kg, at least about 15 mg/kg, at least about 16 mg/kg, at least about 17 mg/kg, at least about 18 mg/kg, at least about 19 mg/kg, and at least about 20 mg/kg.

6. EXAMPLES

Example 1

HuLuc63 in Combination with Dexamethasone

Dexamethasone (Dex) is a corticosteroid that is used extensively for the treatment of MM in multiple lines of therapy. Dex has been used as monotherapy or in combination with a variety of agents, including lenalidomide, thalidomide, velcade or as part of the VAD (vincristine, doxorubicin, dexamethasone) regimen or the DVd liposomal doxorubicin, vincristine, short-schedule dexamethasone regimen. The mechanism of action of Dex involves direct induction of apoptosis of myeloma cells by activation of caspases (Chauhan et al., 1997, Oncogene 15:837-843; Chauhan et al., 1997, J. Biol. Chem. 272, 29995-29997; Chauhan et al., 2001, J. Biol. Chem., 276: 24453-24456).

The effect of HuLuc63 and Dex treatment on the expression of CS1 in MM cell lines and mouse xenograft tumors was examined by flow cytometry and immunohistochemistry respectively.

In vivo Xenograft Mouse Model: Methods and Results

Six- to eight-week old female IcrTac:ICR-Prkdcscid mice obtained from Taconic Farms (Germantown, N.Y.) were inoculated with $1 \times 10^7$ OPM2 or L363 cells (German Collection of Microorganisms and Cell Cultures, Braunschweig, Germany) into the lower right flank. Caliper measurements were performed twice weekly to calculate tumor volume using the following formula: L×W×H/2, where L (length) is the longest side of the tumor in the plane of the animal's back, W (width) is the longest measurement perpendicular to the length and in the same plane and H (height) is taken at the highest point perpendicular to the back of the animal. When tumors reached an average size of about 100 mm³, animals were randomized into 3 groups of 8-10 mice each and were treated with 1 or 10 mg/kg of HuLuc63 or isotype control antibody administered intraperitoneally twice a week for a maximum of 6 doses.

Dex was administered intraperitoneally at a dose of 10 mg/kg twice a week for a maximum of 6 doses.

Tumor growth was monitored for a period of 1-2 months. Animal work was carried out under NIH guidelines ("Guide for the Care and Use of Laboratory Animals") using protocols approved by IACUC at PDL BioPharma.

CS1 protein expression was examined on the OPM2 multiple myeloma cell line. No significant change in CS1 expression was observed pre- or post-treatment with HuLuc63, Dex, or with both agents. The combination of HuLuc63 with Dex was tested for anti-myeloma activity in vivo. OPM2 tumor-bearing mice were treated with sub-optimal doses of HuLuc63 (1 mg/kg), or isotype control antibody twice weekly for three weeks. Dex was given twice a week at 10 mg/kg to mice receiving either isotype control antibody or HuLuc63. The results showed significant anti-tumor activity of HuLuc63 alone and in combination with Dex (see, e.g., FIG. 1). Mice in the combination treatment group exhibited significantly smaller tumors than in the HuLuc63 monotherapy group (see, e.g., FIG. 1).

Example 2

HuLuc63 in Combination with Thalidomide

Thalidomide (Thal) is an immunomodulatory drug that is currently approved for the treatment of MM in combination with Dex. The mechanism of action of Thal is not completely understood, but involves inhibition of angiogenesis, inhibition of growth and survival of stromal cells and tumor cells in the bone marrow, and altering the production of factors that influence the survival of myeloma cells (such as IL-6, IL-10, IL-4, IL-5, IL-12, IL-8, TNF-alpha).

The effect of HuLuc63 and Thal treatment on the expression of CS1 in MM cell lines and mouse xenograft tumors was examined by flow cytometry and immunohistochemistry respectively, as described above.

Figure 2:
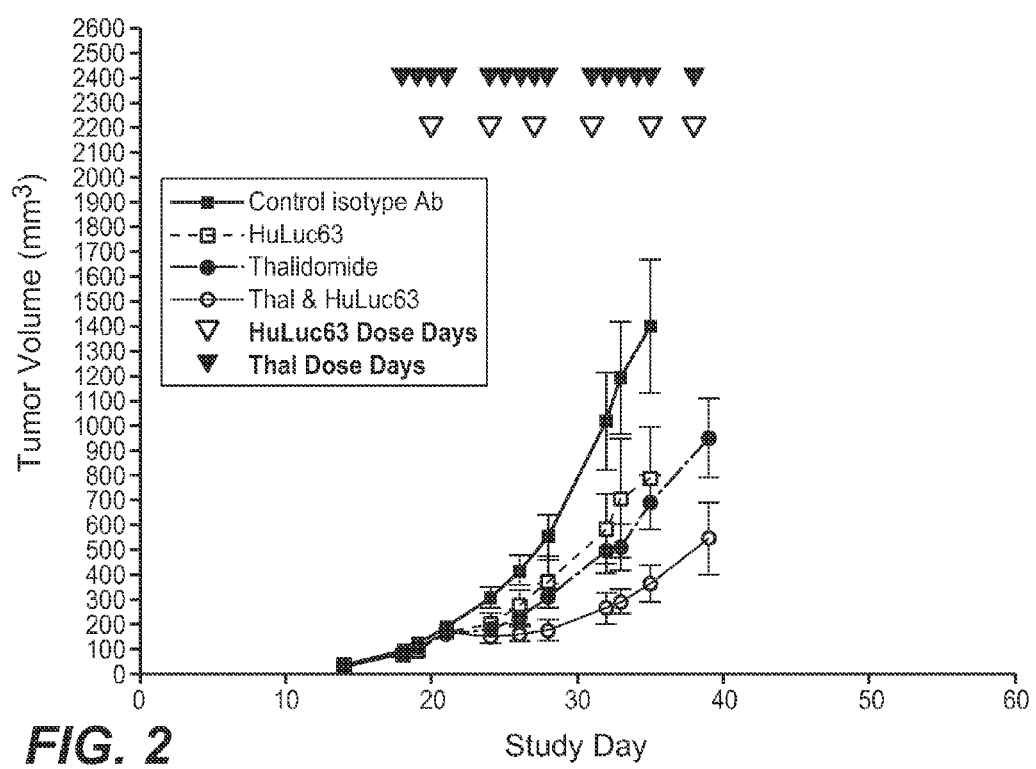
FIG. 2 depicts the anti-tumor activity of HuLuc63 alone, thalidomide alone, and HuLuc63 in combination with thalidomide in an in vivo mouse multiple myeloma xenograft model.

CS1 protein expression was examined on the L363 multiple myeloma cell line. No significant change in CS1 expression was observed pre- or post-treatment with HuLuc63, Thal or with both agents. The combination of HuLuc63 with Thal was tested for anti-myeloma activity in vivo. L363 tumor-bearing mice were treated with HuLuc63, or isotype control antibody twice weekly for three weeks at 10 mg/kg. Thal was given 5 days a week at 50 mg/kg for a maximum of 15 doses to mice receiving either isotype control antibody or HuLuc63. Significant anti-tumor activity was observed with HuLuc63 alone, Thal alone and HuLuc63 in combination with Thal (see, e.g., FIG. 2). Mice in the combination treatment group exhibited smaller tumors compared to the HuLuc63 and Thal monotherapy groups (see, e.g., FIG. 2).

Example 3

HuLuc63 in Combination with Thalidomide/Dexamethasone

Thal/Dex combination therapy is currently approved for front-line treatment of MM patients. The combination of HuLuc63 with Thal/Dex was tested for anti-myeloma activity in vivo as described above. The effect of Thal/Dex treatment on the expression of CS1 in MM cell lines and mouse xenograft tumors was examined by immunohistochemistry as described above.

Figure 3:
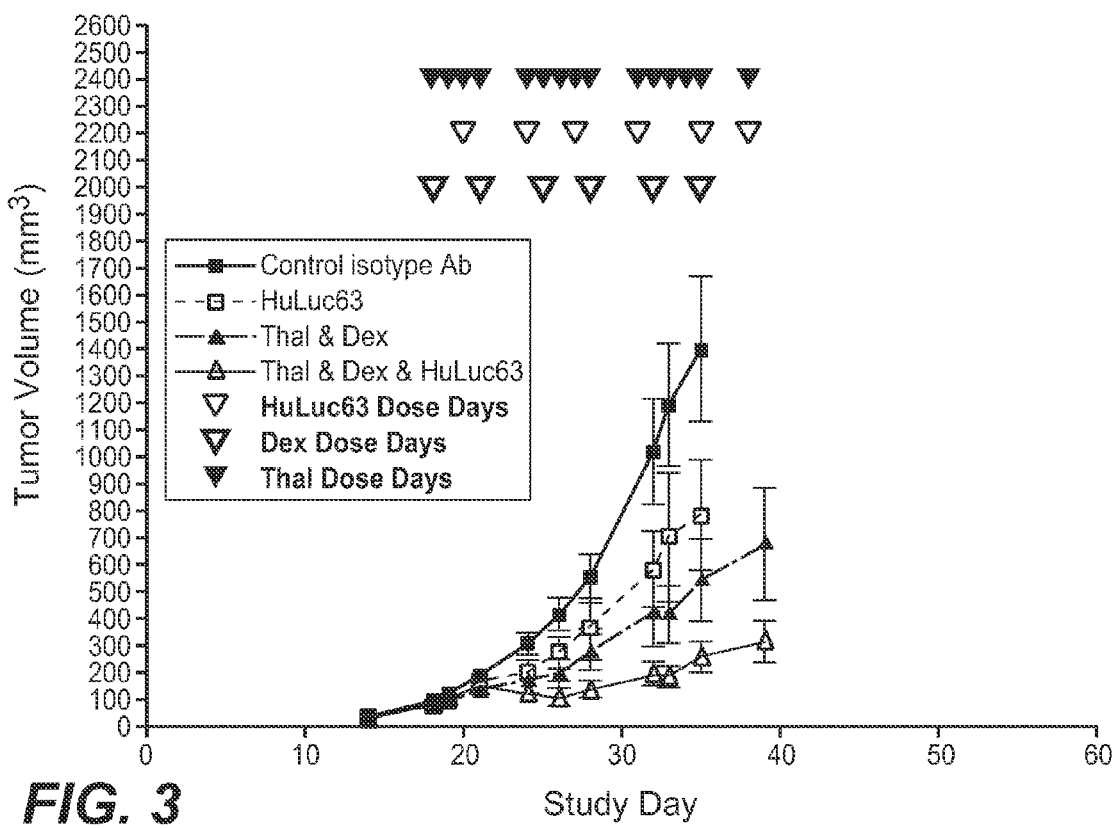
FIG. 3 depicts the anti-tumor activity of HuLuc63 alone, thalidomide/dexamethasone, and HuLuc63 in combination with thalidomide and dexamethasone in an in vivo mouse multiple myeloma xenograft model.

L363 tumor-bearing mice were treated with HuLuc63, or isotype control antibody twice weekly for three weeks at 10 mg/kg. Thal was given 5 days a week at 50 mg/kg for a maximum of 15 doses and Dex was given twice a week at 10 mg/kg for a maximum of 6 doses to mice receiving either isotype control antibody or HuLuc63. The results showed significant anti-tumor activity of HuLuc63 alone, Thal/Dex alone and HuLuc63 in combination with Thal/Dex (see e.g., FIG. 3). Mice in the HuLuc63/Thal/Dex combination treatment group exhibited the smallest tumors, on average exhibiting a decrease of 50-70% in tumor size compared to HuLuc63 monotherapy or Thal/Dex therapy (see e.g., FIG. 3).

Example 4

HuLuc63 in Combination with Bevacizumab

Bevacizumab is a monoclonal antibody that targets the endothelial growth factor VEGF. It works by inhibiting VEGF, resulting in the inhibition of new blood vessel formation in tumors. Bevacizumab is currently approved for the treatment of solid tumors, including metastatic colorectal cancer. Bevacizumab is currently not approved for the use in the treatment of MM.

Figure 4:
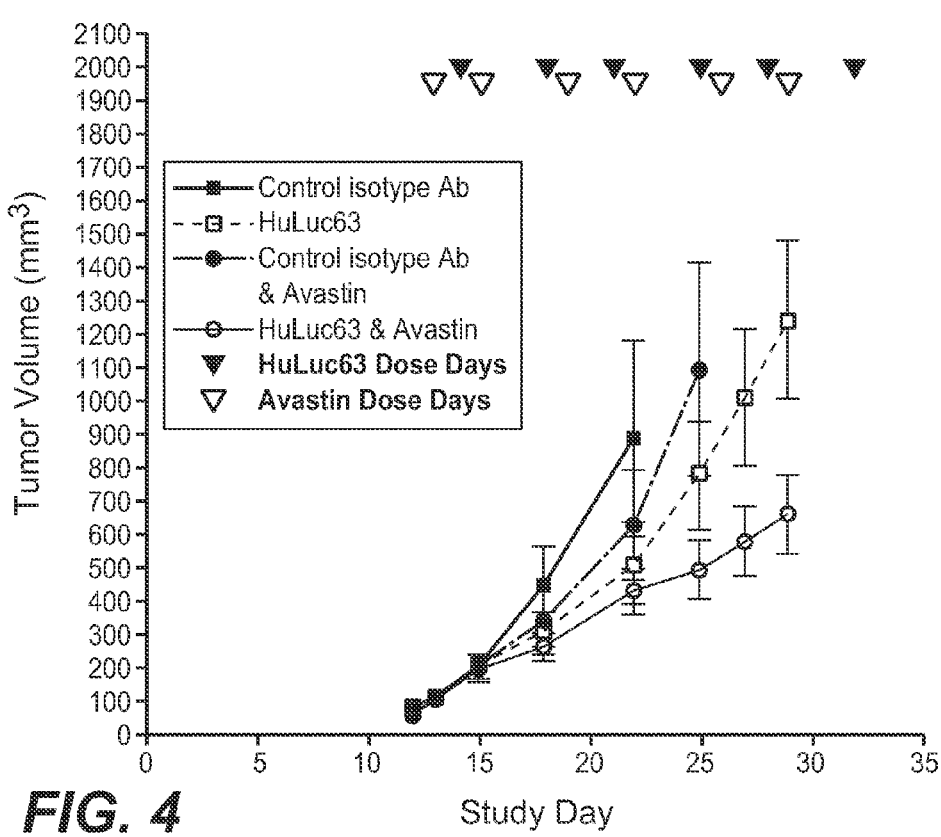
FIG. 4 depicts the anti-tumor activity of HuLuc63 alone and in combination with bevacizumab in an in vivo mouse multiple myeloma xenograft model.

To determine if an anti-angiogenic drug can enhance the antitumor effects of HuLuc63, a combination of HuLuc63 with Bevacizumab was tested for anti-myeloma activity in vivo, as described above. L363 tumor-bearing mice were treated with HuLuc63, or isotype control antibody twice weekly for three weeks at 10 mg/kg. Bevacizumab was given twice a week at 0.5 mg/kg for a maximum of 6 doses to mice receiving either isotype control antibody or HuLuc63. Significant anti-tumor activity of HuLuc63 alone and in combination with Bevacizumab was observed (see e.g., FIG. 4). Bevacizumab alone did not exhibit significant anti-tumor activity. However, mice receiving the combination of HuLuc63 with Bevacizumab exhibited significantly smaller tumors compared to the HuLuc63 monotherapy group, indicating that HuLuc63 and Bevacizumab may act synergistically to cause an anti-myeloma effect.

Example 5

Treatment of Patients Diagnosed with Multiple Myeloma

Proposed multi-center, open-label, multi-dose, dose escalation studies will be used to evaluate the combination of HuLuc63 and one or more therapeutic agents in patients with multiple myeloma after $1^{st}$, $2^{nd}$, or $3^{rd}$ relapse. HuLuc63 will be given by intravenous injection (IV) at up to five dose levels ranging from 2.5 mg/kg to 20 mg/kg in combination with one or more therapeutic agents. Patients will receive HuLuc63 once a week, with each dose infused over 1 hour, once every 10 days or once every two weeks, for a minimum of 4 doses and a maximum of 52 doses.

Drug combinations suitable for administration with HuLuc63 include, but are not limited to:

1) Melphalan+prednisone. Melphalan will be given in 28 day cycles, at 8 $mg/m^2/d$ on days 1 to 4, for a maximum number of 11 cycles. Prednisone will be given will be given in 28 day cycles, at 60 $mg/m^2/d$ on days 1 to 4, for a maximum number of 11 cycles;

2) Melphalan+prednisone+thalidomide. Melphalan will be given in 28 day cycles, at 8 $mg/m^2/d$ on days 1 to 4, for a maximum number of 11 cycles. Prednisone will be given will be given in 28 day cycles, at 60 $mg/m^2/d$ on days 1 to 4, for a maximum number of 11 cycles. Thalidomide will be given in 28 day cycles, at 200 mg/d, for a maximum number of 11 cycles;

3) Melphalan+prednisone+lenalidomide. Melphalan will be given in 28 to 42 day cycles, at 0.18 to 0.25 mg/kg for 4 days every 4 to 6 weeks, for a maximum number of 9 cycles. Prednisone will be given will be given in 28 to 42 day cycles, at 2 mg/kg for 4 days every 4 to 6 weeks, for a maximum number of 9 cycles. Lenalidomide will be given in 28 to 42 day cycles, at 5 to 10 mg/day, days 1 to 21 every 4 to 6 weeks, for a maximum number of 9 cycles;

4) Melphalan+prednisone+bortezomib. Melphalan will be given in 42 day cycles, at 9 $mg/m^2/day$ on days 1 to 4, for a maximum number of 4 cycles. Prednisone will be given will be given in 42 day cycles, 60 $mg/m^2/d$ on days 1 to 4, for a maximum number of 4 cycles. Bortezomib will be given in 42 day cycles, at 1.3 $mg/m^2/day$ on days 1, 4, 8, 11, 22, 25, 29 and 32, for a maximum number of 4 cycles;

5) Thalidomide+dexamethasone. Thalidomide will be given in 28 day cycles, at 200 mg/d, for a maximum number of 4 to 12 cycles. Dexamethasone will be given at 40 mg/day on days 1 to 4, 9 to 12, and 17 to 20, for a maximum number of 4 to 12 cycles;

6) Cytoxan+prednisone. Cytoxan will be given in 28 day cycles, at 500 mg, once weekly, for a maximum number of 6 cycles. Prednisone will be given in 28 day cycles, at 100 mg/day, every other day, for a maximum number of 6 cycles;

7) Cytoxan+prednisone+thalidomide. Cytoxan will be given in 28 day cycles, at 50 mg twice per day for 21 days, for a maximum number of 7 cycles. Prednisone will be given in 28 day cycles, at 100 mg/day, every other day, for a maximum number of 7 cycles. Thalidomide will be given in 28 day cycles, at 200 mg/d, for a maximum number of 7 cycles;

8) Cytoxan+prednisone+lenalidomide. Cytoxan will be given in 28 day cycles, at 300 to 700 mg on days 1 and 8, for a maximum number of 4 to 7 cycles. Prednisone will be given in 28 day cycles, at 50 mg/day every other day, for a maximum number of 4 to 7 cycles. Lenalidomide will be given in 28 day cycles, at 25 mg/day on days 1 to 21, for a maximum number of 4 to 7 cycles;

9) Cytoxan+dexamethasone+lenalidomide. Cytoxan will be given in 28 day cycles, at 300 to 700 mg on days 1 and 8, for a maximum number of 4 to 7 cycles. Dexamethasone will be given in 28 day cycles, at 40 mg on days 1 to 4, 9 to 12 and 17 to 20, for a maximum number of 4 to 7 cycles. Lenalidomide will be given in 28 day cycles, at 25 mg/day on days 1 to 21, for a maximum number of 4 to 7 cycles;

10) Cytoxan+prednisone+bortezomib. Cytoxan will be given in 28 day cycles, at 300 mg on days 1, 8, 15, and 22, for a maximum number of 4 to 7 cycles. Prednisone will be given in 28 day cycles, at 100 mg every other day, for a maximum number of 4 to 7 cycles. Bortezomib will be given in 28 day cycles, at 1.5 $mg/m^2/day$, days 1, 8, and 15, for a maximum number of 4 to 7 cycles;

11) Bevacizumab. Bevacizumab will be given in 14 day cycles, at 5 mg/kg, every 2 weeks, for a maximum number of 6 to 26 cycles;

12) Tanespimycin+bortezomib. Tanespimycin will be given in 21 day cycles, at 100 to 340 $mg/m^2$, twice weekly for 2 weeks, for a maximum of 4 to 8 cycles. Bortezomib will be given in 21 day cycles, at 0.7 to 1.3 $mg/m^2$, twice weekly for 2 weeks, for a maximum number of 4 to 8 cycles;

13) Doxil+bortezomib. Doxil will be given in 21 day cycles, at 30 $mg/m^2/day$, at day 4, for a maximum number of 4 to 8 cycles. Bortezomib will be given in 21 day cycles, at 1.3 $mg/m^2$, days 1, 4, 8 and 11, for a maximum number of 4 to 8 cycles; and, 14) Dexamethasone. Dexamethasone can be given in 28 day cycles, at 40 mg/day, at days 1 to 4, 9 to 12, and 17 to 20, for a maximum number of 4 to 12 cycles, or alternately, in 28 day cycles, at 40 mg/day for 4 days, in 28 day cycles.

The above drug combinations can be given orally or by IV.

After 8-12 weeks of therapy, EBMT criteria will be assessed. If a patient has progressive disease, HuLuc63 will be discontinued and the other drug combinations may be withdrawn or continued at the discretion of the site investigator. If the patient has responded or has stable disease at Week 8-12, dosing with HuLuc63 and the drug combination will continue so that a maximum of 52 weeks of treatment are completed or disease progression occurs.

Approximately 15 to 30 patients in 5 cohorts will be enrolled for each drug combination. Each cohort will begin with 3 patients. If no dose-limiting toxicity (DLT) is noted within the first 4 weeks of treatment in any patient, enrollment will begin in the next higher cohort. If one patient has a DLT, 3 additional patients will be enrolled in the cohort. If no other patient in the cohort has a DLT, escalation to the next cohort may proceed. If a second patient in a cohort has a DLT, the maximum tolerated dose (MTD) has been reached.

A dose-limiting toxicity (DLT) is defined using the National Cancer Center Institute Common Toxicity Criteria Version 3.0 (NCI CTCAE v3.0) as a grade 4 hematologic toxicity or hyperbilirubinemia, or a grade 3 toxicity in any other system considered related to HuLuc63 or the combination of HuLuc63 and any of the drugs listed in Table 1. For dose escalation to the next cohort, 3 assessable patients must complete their first 4 weeks of dosing. If a DLT occurs, an additional three assessable patients will be accrued. Patients will be monitored for safety by assessing adverse events categorized by NCI CTCAE v3.0 and patients will be monitored for clinical activity using EBMT. The maximally tolerated dose (MTD) is defined as the highest dose studied for which the incidence of DLTs is <33%. The highest tolerated dose will be HuLuc63 at 20 mg/kg combined with the drugs at the doses listed above if no dose limiting toxicities are observed.

DEPOSIT OF PLASMID: Plasmid pHuLuc63 encoding the heavy and light chains of the monoclonal antibody HuLuc63 was deposited with the American Type Culture Collection ("ATCC"), at 10801 University Blvd., Manassas, Va. 20510-209, U.S., on May 25, 2010, in compliance with the Budapest Treaty on the International Recognition of the Deposit of Microorganisms for the Purposes of Patent Procedure on behalf of Facet Biotech Corporation, having a place of business at 1400 Seaport Blvd., Redwood City, Calif. 94063, present assignee of the application. The plasmid was assigned ATCC accession number PTA-10989.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of treating multiple myeloma in a subject, the method comprising administering to a subject in need thereof (a) HuLuc63, said HuLuc63 being a humanized $IgG_1$ antibody having a heavy chain variable region corresponding to SEQ ID NO:5 and a light chain variable region corresponding to SEQ ID NO:6, and constant regions encoded by the plasmid pHuLuc63 as deposited with the American Type Culture Collection ("ATCC") and assigned ATCC deposit no. PTA-10989, and (b) one or more therapeutic agents, wherein said one or more therapeutic agents consist of dexamethasone and, optionally, thalidomide.

2. The method of claim 1, in which HuLuc63 is administered intravenously at a dosage from approximately 0.5 mg/kg to approximately 20 mg/kg.

3. The method of claim 1, in which HuLuc63 is administered concurrently with said dexamethasone and, optionally, with said thalidomide.

4. The method of claim 3, in which said administration elicits a complete response as defined by the European Group for Blood and Marrow Transplantation ("EMBT").

5. The method of claim 3, in which said administration elicits a greater than 90% decrease in M protein.

6. The method of claim 3, in which said administration elicits a partial response as defined by EMBT.

7. The method of claim 3, in which said administration elicits a minimal response as defined by EMBT.

* * * * *

SEQUENCE LISTING

<160> NUMBER OF SEQ ID NOS: 6

<210> SEQ ID NO 1
<211> LENGTH: 335
<212> TYPE: PRT
<213> ORGANISM: Homo sapiens

<400> SEQUENCE: 1

```
Met Ala Gly Ser Pro Thr Cys Leu Thr Leu Ile Tyr Ile Leu Trp Gln
 1               5                  10                  15

Leu Thr Gly Ser Ala Ala Ser Gly Pro Val Lys Glu Leu Val Gly Ser
            20                  25                  30

Val Gly Gly Ala Val Thr Phe Pro Leu Lys Ser Lys Val Lys Gln Val
        35                  40                  45

Asp Ser Ile Val Trp Thr Phe Asn Thr Thr Pro Leu Val Thr Ile Gln
    50                  55                  60

Pro Glu Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
        115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
        195                 200                 205

Ile Leu Ala Arg Lys Leu Cys Glu Gly Ala Ala Asp Asp Pro Asp Ser
    210                 215                 220

Ser Met Val Leu Leu Cys Leu Leu Val Pro Leu Leu Leu Ser Leu
225                 230                 235                 240

Phe Val Leu Gly Leu Phe Leu Trp Phe Leu Lys Arg Glu Arg Gln Glu
                245                 250                 255
```

-continued

Glu Tyr Ile Glu Glu Lys Lys Arg Val Asp Ile Cys Arg Glu Thr Pro
                260                 265                 270

Asn Ile Cys Pro His Ser Gly Glu Asn Thr Glu Tyr Asp Thr Ile Pro
            275                 280                 285

His Thr Asn Arg Thr Ile Leu Lys Glu Asp Pro Ala Asn Thr Val Tyr
        290                 295                 300

Ser Thr Val Glu Ile Pro Lys Lys Met Glu Asn Pro His Ser Leu Leu
305                 310                 315                 320

Thr Met Pro Asp Thr Pro Arg Leu Phe Ala Tyr Glu Asn Val Ile
                325                 330                 335

<210> SEQ ID NO 2
<211> LENGTH: 227
<212> TYPE: PRT
<213> ORGANISM: Artificial
<220> FEATURE:
<223> OTHER INFORMATION: hu50/mu50

<400> SEQUENCE: 2

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
            20                  25                  30

Val Gly Gly Ala Val Thr Phe Pro Leu Lys Ser Lys Val Lys Gln Val
        35                  40                  45

Asp Ser Ile Val Trp Thr Phe Asn Thr Pro Leu Val Thr Ile Gln
    50                  55                  60

Pro Glu Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
        115                 120                 125

Ser Lys Pro Lys Val Thr Ile Asp Arg Gln Ser Asn Lys Asn Gly Thr
    130                 135                 140

Cys Val Ile Asn Leu Thr Cys Ser Thr Asp Gln Asp Gly Glu Asn Val
145                 150                 155                 160

Thr Tyr Ser Trp Lys Ala Val Gly Gln Gly Asp Asn Gln Phe His Asp
                165                 170                 175

Gly Ala Thr Leu Ser Ile Ala Trp Arg Ser Gly Glu Lys Asp Gln Ala
            180                 185                 190

Leu Thr Cys Met Ala Arg Asn Pro Val Ser Asn Ser Phe Ser Thr Pro
        195                 200                 205

Val Phe Pro Gln Lys Leu Cys Glu Asp Ala Ala Thr Asp Leu Thr Ser
    210                 215                 220

Leu Arg Gly
225

<210> SEQ ID NO 3
<211> LENGTH: 227
<212> TYPE: PRT
<213> ORGANISM: Artificial
<220> FEATURE:
<223> OTHER INFORMATION: mu25/hu75

<400> SEQUENCE: 3

```
Met Ala Arg Phe Ser Thr Tyr Ile Ile Phe Thr Ser Val Leu Cys Gln
1               5                   10                  15

Leu Thr Val Thr Ala Ala Ser Gly Thr Leu Lys Lys Val Ala Gly Ala
            20                  25                  30

Leu Asp Gly Ser Val Thr Phe Thr Leu Asn Ile Thr Glu Ile Lys Val
                35                  40                  45

Asp Tyr Val Val Trp Thr Phe Asn Thr Phe Phe Leu Ala Met Val Lys
            50                  55                  60

Lys Asp Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
                100                 105                 110

Gln Gln Pro Ser Thr Gln Glu Tyr Val Leu His Val Tyr Glu His Leu
            115                 120                 125

Ser Lys Pro Lys Val Thr Met Gly Leu Gln Ser Asn Lys Asn Gly Thr
            130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
                180                 185                 190

Phe Ile Cys Val Ala Arg Asn Pro Val Ser Arg Asn Phe Ser Ser Pro
            195                 200                 205

Ile Leu Ala Arg Lys Leu Cys Glu Gly Ala Ala Asp Asp Pro Asp Ser
            210                 215                 220

Ser Met Val
225

<210> SEQ ID NO 4
<211> LENGTH: 224
<212> TYPE: PRT
<213> ORGANISM: Artificial
<220> FEATURE:
<223> OTHER INFORMATION: mu75/hu25

<400> SEQUENCE: 4

Met Ala Arg Phe Ser Thr Tyr Ile Ile Phe Thr Ser Val Leu Cys Gln
1               5                   10                  15

Leu Thr Val Thr Ala Ala Ser Gly Thr Leu Lys Lys Val Ala Gly Ala
            20                  25                  30

Leu Asp Gly Ser Val Thr Phe Thr Leu Asn Ile Thr Glu Ile Lys Val
                35                  40                  45

Asp Tyr Val Val Trp Thr Phe Asn Thr Phe Phe Leu Ala Met Val Lys
            50                  55                  60

Lys Asp Gly Val Thr Ser Gln Ser Ser Asn Lys Glu Arg Ile Val Phe
65                  70                  75                  80

Pro Asp Gly Leu Tyr Ser Met Lys Leu Ser Gln Leu Lys Lys Asn Asp
                85                  90                  95

Ser Gly Ala Tyr Arg Ala Glu Ile Tyr Ser Thr Ser Ser Gln Ala Ser
                100                 105                 110

Leu Ile Gln Glu Tyr Val Leu His Val Tyr Lys His Leu Ser Arg Pro
            115                 120                 125

Lys Val Thr Ile Asp Arg Gln Ser Asn Lys Asn Gly Thr Cys Val Ile
```

130                 135                 140
Asn Leu Thr Cys Ser Thr Asp Gln Asp Gly Glu Asn Val Thr Tyr Ser
145                 150                 155                 160

Trp Lys Ala Val Gly Gln Ala Ala Asn Glu Ser His Asn Gly Ser Ile
                165                 170                 175

Leu Pro Ile Ser Trp Arg Trp Gly Glu Ser Asp Met Thr Phe Ile Cys
                180                 185                 190

Val Ala Arg Asn Pro Val Ser Arg Asn Phe Ser Ser Pro Ile Leu Ala
                195                 200                 205

Arg Lys Leu Cys Glu Gly Ala Ala Asp Asp Pro Asp Ser Ser Met Val
                210                 215                 220

<210> SEQ ID NO 5
<211> LENGTH: 119
<212> TYPE: PRT
<213> ORGANISM: Homo sapiens

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Ile
                35                  40                  45

Gly Glu Ile Asn Pro Asp Ser Ser Thr Ile Asn Tyr Ala Pro Ser Leu
            50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
                100                 105                 110

Thr Leu Val Thr Val Ser Ser
            115

<210> SEQ ID NO 6
<211> LENGTH: 107
<212> TYPE: PRT
<213> ORGANISM: Homo sapiens

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Ala
                20                  25                  30

Val Ala Trp Tyr Gln Gln Lys Pro Gly Lys Val Pro Lys Leu Leu Ile
                35                  40                  45

Tyr Trp Ala Ser Thr Arg His Thr Gly Val Pro Asp Arg Phe Ser Gly
            50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Tyr Pro Tyr
                85                  90                  95

Thr Phe Gly Gln Gly Thr Lys Val Glu Ile Lys
                100                 105